United States Patent [19]
Morgan, Jr.

[11] Patent Number: 4,599,344
[45] Date of Patent: Jul. 8, 1986

[54] QUINUCLIDINES AND QUINUCLIDINIUM SALTS AS ANTIARRHYTHMIC AGENTS

[75] Inventor: Thomas K. Morgan, Jr., Morris Plains, N.J.

[73] Assignee: Schering A.G., Berlin, Fed. Rep. of Germany

[21] Appl. No.: 666,788

[22] Filed: Oct. 31, 1984

[51] Int. Cl.<sup>4</sup> .................. A61K 31/445; C07D 453/02
[52] U.S. Cl. .................................... 514/305; 546/133; 546/137
[58] Field of Search ................. 546/133, 137; 514/305

[56] References Cited

U.S. PATENT DOCUMENTS 3,726,877  4/1973  Elkin et al. ........................... 546/137
4,125,531 11/1978  Yen .................................. 546/137 X
4,531,967  7/1985  Van Heertum et al. ........ 546/137 X

FOREIGN PATENT DOCUMENTS 1072248 12/1959  Fed. Rep. of Germany ...... 546/137
2323303 12/1973  Fed. Rep. of Germany ...... 546/133

OTHER PUBLICATIONS

Bondarenko, V., et al., *Khim. Geterotsikl. Soedin* (10), 1387-91 (1981).
Naming and Indexing of Chemical Substances for Chemical Abstracts, Appendix IV, 1982, Index Guide, Chemical Abstracts Service, p. 168I.

*Primary Examiner*—Richard A. Schwartz
*Attorney, Agent, or Firm*—Elizabeth A. Bellamy; Anthony J. Zelano; I. William Millen

[57] ABSTRACT

Novel quinuclidines, their acid addition, quaternary ammonium and inner salts are described. Also provided is the method of using these compounds as antiarrhythmic agents and pharmaceutical formulations containing such compounds.

39 Claims, No Drawings

QUINUCLIDINES AND QUINUCLIDINIUM SALTS AS ANTIARRHYTHMIC AGENTS

PRIOR ART

The novel compounds described herein are potent antiarrhythmic agents. The closest prior art compounds are 2-(2-benzoyl-3-oxobutyl)-3-oxoquinuclidine and 2-(2-benzoylethyl)-3-oxoquinuclidine described by Bondarenko et al. in Khim. Geterotsikl. Soedin (10) 1387–91 (1981). No biological activity is attributed to these compounds and indeed when they were tested in the screens appropriate to demonstrate antiarrhythmic activity, they elicited little or no activity.

FIELD OF THE INVENTION

This invention relates to novel quinuclidines and quinuclidinium salts, which compounds are useful in the treatment of mammalian arrhythmic conditions.

More specifically, this invention relates to substituted quinuclidines, i.e. 2 or 3 or 2 and 3 substituted compounds and their pharmaceutically acceptable acid addition salts, certain quaternary ammonium salts and certain inner salts. The invention also relates to pharmaceutical compositions containing said compounds as active agents and to the method of using them as antiarrhythmic agents.

GENERAL DESCRIPTION OF THE INVENTION

Composition-of Matter Aspect

In its composition-of-matter aspect this invention relates to novel quinuclidines, their pharmaceutically acceptable acid addition salts, quaternary ammonium salts and their inner salts.

Particularly, this invention relates to novel compounds defined by the following Formula I

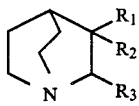

wherein
$R_1$ is H or OH;
$R_2$ is H or ALK—Z;
$R_1$, $R_2$ taken together form =O or =CH—ALK'—Z;
$R_3$ is H or —ALK"—Z;
where
ALK is a straight chain alkyl of 2–4 carbon atoms;
ALK' is a straight chain alkyl of 1–3 carbon atoms;
ALK" is a straight chain alkyl of 1–4 carbon atoms,

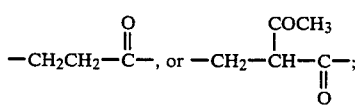

Z is

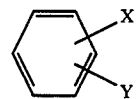

where X and Y are the same or independently hydrogen, halogen, hydroxyl, loweralkyl, loweralkoxy, amino, cyano, nitro, loweralkanecarboxamido, loweralkanesulfonamido carbamoyl, loweralkylcarbamoyl, loweralkylsulfonyl, sulfamoylamino, N-loweralkylsulfamoyl, trifluoromethanesulfonamido, ureido or N-loweralkylureido;
with the provisos that:
(a) X and Y cannot both be hydrogen,
(b) $R_2$ and $R_3$ cannot both be hydrogen,
(c) when $R_3$ is —ALK"—Z wherein the ALK" is —$CH_2$—CH($COCH_3$)—CO— or —$CH_2CH_2CO$— then together $R_1$ and $R_2$ must be =O,
(d) when $R_3$ is —ALK"—Z wherein the ALK" is a straight chain alkyl of 1–4 carbon atoms then $R_2$ cannot be —ALK—Z, and $R_1$, $R_2$ together cannot be =CH—ALK'—Z, or a pharmaceutically acceptable acid addition salt thereof.

Or, the invention is inclusive of a quaternary ammonium salt thereof of the Formula II

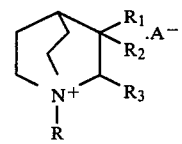

wherein $R_1$, $R_2$, and $R_3$ are as previously defined and R is a straight or branched chain alkyl of 1–12 carbon atoms, cycloalkyl(lower)alkyl, phenyl(lower)alkyl, —$CH_2CHOHCH_2W$, —$(CH_2)_m$—W or —$(CH_2)_m$—$SO_3H$;
where
m is an integer of 1–5, and
W is defined as —COO—V,
where V is hydrogen or a straight or branched chain alkyl of 1–4 carbon atoms,
with the proviso that when R is a straight or branched chain alkyl, the carbon atom alpha to the nitrogen is primary, and A is an anion forming a pharmaceutically acceptable salt;
or the inner salt of Formula II, formed when the anion A is R when R is —CH—CHOH—CHCOO$^-$, —$(CH_2)_m$—COO$^-$ or —$(CH_2)_mSO_3^-$,
where m is as previously described.

Among the compounds as defined by Formulae I and II there exist sites for stereo or geometric isomers by mixture of asymmetric carbon atoms or olefinic linkages. Any of the optical and cis/trans isomers so possible are considered to be part of this invention.

As used herein the term halogen is defined as fluorine, chlorine, bromine or iodine. The terms loweralkyl, loweralkoxy, lower "alkan" are taken to mean straight or branched chains containing 1–4 carbon atoms. Cycloalkyl shall refer to a carbocylic ring containing 3 to 6 carbon atoms. When A⁻ is a pharmaceutically acceptable anion it shall be taken to mean, but not limited to, chloride, bromide, hydrogen sulfate, dihydrogen phosphate or methanesulfonate.

Also contemplated as part of this invention are the pharmaceutically acceptable acid addition salts of the compounds of Formula I. These acid addition salts may be formed with inorganic or organic acids. Illustrative but not restrictive examples of such acids include hydrochloric, hydrobromic, sulfuric, phosphoric, acetic, benzoic, methanesulfonic, and 2-hydroxyethanesulfonic acid.

Preferred classes of compounds embodied by this invention are those of the above general Formulae I and II having one of the following characteristics:

(a) where $R_1$ and $R_2$ together form =O,
(b) where $R_3$ is —ALK″—Z,
(c) where X and Y are the same or independently hydrogen, halogen, hydroxyl, loweralkoxy, loweralkanesulfonamido or N-loweralkylureido.

The more preferred compounds of this invention are those wherein $R_1$ and $R_2$ together form =O, $R_3$ is —ALK″—Z, and X and Y are the same or independently hydrogen, halogen, hydroxyl, loweralkoxy, loweralkanesulfonamido or N-loweralkylureido.

Still more preferred compounds of this invention are those wherein $R_1$ and $R_2$ together form =O, and $R_3$ is —ALK″—Z wherein —ALK″—Z is —CH₂CH₂—CH₂—Z or

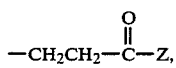

and wherein X and Y are the same or independently hydrogen, halogen, or loweralkanesulfonamido. Of these compounds the most preferred are those wherein halogen is defined as chlorine and loweralkanesulfonamido is defined as methanesulfonamido. Most especially preferred compounds are those wherein one of X or Y is chlorine or methanesulfonamido and is located in the para position of the phenyl ring.

The compounds which follow serve to exemplify some of the composition-of-matter aspects of the invention described herein.

(1) 3-[2-(4-Chlorophenyl)ethylidene]-1-azabicyclo[2.2.2]-octane hydrochloride.
(2) 3-[2-(4-Chlorophenyl)ethylidene]-1-heptyl-1-azoniabicyclo[2.2.2]octane bromide.
(3) 3-[2-(4-Chlorophenyl)ethyl]-1-heptyl-1-azoniabicyclo[2.2.2]octane bromide.
(4) 2-[3-(4-Chlorophenyl)propyl]-1-azabicyclo[2.2.2]octan-3-ol.
(5) 2-[3-(4-Chlorophenyl)propyl]-1-azabicyclo[2.2.2]octane hydrochloride.
(6) 3-[2-(4-Chlorophenyl)ethylidene]-1-[3-((1,1-dimethylethoxy)carbonyl)-2-hydroxypropyl]-1-azoniabicyclo[2.2.2]octane chloride.
(7) 3-[2-(4-Chlorophenyl)ethyl]-1-azabicyclo[2.2.2]octane hydrochloride.
(8) 3-[2-(4-Chlorophenyl)ethylidene]-1-methyl-1-azoniabicyclo[2.2.2]octane bromide.
(9) 3-[2-(4-Chlorophenyl)ethylidene]-1-(3-sulfopropyl)-1-azoniabicyclo[2.2.2]octane hydroxide, inner salt.
(10) 1-(3-Carboxy-2-hydroxypropyl)-3-[2-(4-chlorophenyl)ethylidene]-1-azoniabicyclo[2.2.2]octane hydroxide, inner salt.
(11) 3-[2-(4-Nitrophenyl)ethylidene]-1-azabicyclo[2.2.2]octane hydrochloride.
(12) 3-[2-(4-Aminophenyl)ethylidene]-1-azabicyclo[2.2.2]octane dihydrochloride.
(13) N-[4-(2-(1-Azabicyclo[2.2.2]oct-3-ylidene)ethyl)phenyl]methanesulfonamide hydrochloride.
(14) 3-[2-(4-((Methylsulfonyl)amino)phenyl)ethylidene]-1-heptyl-1-azoniabicyclo[2.2.2]octane bromide.
(15) 3-[2-(4-Chlorophenyl)ethyl]-1-azabicyclo[2.2.2]octan-3-ol hydrochloride.
(16) 3-[2-(4-Chlorophenyl)ethyl]-1-heptyl-3-hydroxyl-1-azoniabicyclo[2.2.2]octane bromide.
(17) 2-[3-(4-Nitrophenyl)propyl]-1-azabicyclo[2.2.2]octane hydrochloride.
(18) 2-[3-(4-Aminophenyl)propyl]-1-azabicyclo[2.2.2]octane dihydrochloride.
(19) N-[4-(3-(1-Azabicyclo[2.2.2]oct-2-yl)propyl)phenyl]methanesulfonamide hydrochloride.
(20) 1-Heptyl-2-[3-(4-((methylsulfonyl)amino)phenyl)propyl]-1-azoniabicyclo[2.2.2]octane bromide.
(21) 2-[3-(4-Nitrophenyl)propyl]-1-azabicyclo[2.2.2]octan-3-one hydrochloride.
(22) 2-[3-(4-Aminophenyl)propyl]-1-azabicyclo[2.2.2]octan-3-one dihydrochloride.
(23) 1-(4-Chlorophenyl)-2-[(3-oxo-1-azabicyclo[2.2.2]oct-2-yl)methyl]-1,3-butanedione hydrochloride.
(24) N-[4-(3-(3-Oxo-1-azabicyclo[2.2.2]octan-2-yl) propyl)-phenyl]methanesulfonamide hydrochoride.
(25) 1-Heptyl-2-[3-(4-((methylsulfonyl)amino)phenyl)-propyl]-3-oxo-1-azoniabicyclo[2.2.2]octane bromide.
(26) N-[2-Chloro-5-[3-(3-oxo-1-azabicyclo[2.2.2]oct-2-yl)-1-oxopropyl]phenyl]methanesulfonamide hydrochloride.
(27) 2-[3-(4-Chlorophenyl)-3-oxopropyl]-1-azabicyclo[2.2.2]-octan-3-one hydrochloride.
(28) 2-[3-(4-Chlorophenyl)propyl]-1-azabicyclo[2.2.2]octan-3-one hydrochloride.
(29) 1-Heptyl-2-[3-(4-chlorophenyl)propyl]-3-oxo-1-azoniabicyclo[2.2.2]octane dihydrogen phosphate.
(30) 2-[3-(3,5-Dimethoxyphenyl)-3-oxopropyl]-1-azabicyclo[2.2.2]octan-3-one hydrochloride.
(31) 3-[2-(2,3-Dichlorophenyl)ethylidene]-1-methyl-1-azoniabicyclo[2.2.2]octane bromide.
(32) 1-(4-Chloro-3-nitrophenyl)-2-[(3-oxo-1-azabicyclo[2.2.2]oct-2-yl)methyl]1,3-butanedione hydrochloride.
(33) 2-[3-(4-Chloro-3-nitrophenyl)-3-oxopropyl]-1-azabicyclo[2.2.2]octan-3-one hydrochloride.
(34) 2-[3-(3-Amino-4-chlorophenyl)-3-oxopropyl]-1azabicyclo-[2.2.2]octan-3-one dihydrochloride.
(35) 2-[3-(4-Chloro-3-((methylamino)carbonylamino)phenyl)-3-oxopropyl]-1-azabicyclo[2.2.2]ocan-3-one hydrochloride.
(36) 1-(4-Nitrophenyl)-2-[(3-oxo-1-azabicyclo[2.2.2]oct-2-yl)methyl]-1,3-butanedione hydrochloride.
(37) 2-[3-(4-Nitrophenyl)-3-oxopropyl]-1-azabicyclo[2.2.2]octan-3-one hydrochloride.

PROCESS ASPECT

The compounds of this invention may be prepared in general, by various processes using reactants known in the art.

Via one route in order to prepare a 3-[(un)substituted phenylalkylidene]quinuclidine, an (un)substituted phenylalkyltriphenylphosphonium salt is converted to the corresponding (un)substituted phenylalkylenetriphenylphosphorane by the addition of one equivalent of a solution of n-butyl lithium in a suitable solvent (e.g. hexane) to a cold solution or suspension of one equivalent of the phosphonium salt in a suitable solvent (e.g. tetrahydorfuran, diethyl ether, dimethoxyethane) under a nitrogen or argon atmosphere. The reaction mixture is stirred for about 1 to 2 hours to complete the formation of the phosphorane. Then one equivalent of 3-quinuclidinone in a suitable solvent (e.g. tetrahydrofuran, diethyl ether, dimethoxyethane) is added to the reaction mixture. The reaction mixture is stirred for about 1 to 4 hours, the progress being monitored by thin-layer chromatography. When the reaction is completed, excess reagent is quenched with methanol, the solvent is removed in vacuo and the residue is suspended in water with stirring. This residue is acidified to pH=1 and then extracted with several portions of a suitable solvent (e.g. ethyl acetate, methylene chloride, toluene). The aqueous extract is made alkaline to pH 12-13 with aqueous sodium hydroxide and extracted with a suitable solvent (e.g. ethyl acetate, methylene chloride, toluene). Evaporation of the solvent after drying over sodium sulfate produces the requisite 3-[((un)substituted phenyl)alkylidene]quinuclidine.

In yet another route for the preparation of the foregoing compounds: to a cold (−10° to 0° C.) solution of 1 equivalent of a diethyl (un)substituted phenylalkylphosphonate in a suitable solvent (e.g. tetrahydrofuran, diethyl ether, dimethoxyethane) is added 1 equivalent of a solution of n-butyl lithium in a solvent such as hexane under an atmosphere of nitrogen. Stir the cold solution for about 1 to 2 hours to complete formation of the anion. To the solution of the anion is added 1 equivalent of 3-quinuclidinone (either as a solid or dissolved in the reaction solvent). Stir the reaction for 1 to 4 hours and allow it to warm to room temperature, the progress of the reaction is followed by thin-layer chromatography. When complete, the reaction mixture is quenched with methanol. After removal of the solvent in vacuo, the residue is suspended in water (or other solvent such as methanol, ethanol or 2-propanol) with stirring. The mixture is acidified with a suitable acid (e.g. hydrochloric, hydrobromic, sulfuric). The 3-[((un)substituted phenyl)alkylidene]quinuclidine is collected by filtration as its acid addition salt.

The formation of 3-hydroxy-3-[((un)substituted phenyl)alkyl]quinuclidines can be accomplished via a Grignard reaction. That is, an [(un)substituted phenyl]alkyl halide is reacted to form a Grignard reagent and then further reacted with 3-quinuclidinone to form the desired compound.

Preparation of 3-[((un)substituted phenyl)alkyl]quinuclidines is afforded by hydrogenation of the appropriate 3-[((un)substituted phenyl)alkylidene)quinuclidine. Said hydrogenation is carried out in a manner according to the art and compound involved. The usual hydrogenation catalysts are palladium on carbon or platinum oxide.

In order to prepare a 2-(substituted phenyl)alkyl quinuclidin-3-one wherein an —ALK″— is present as defined by

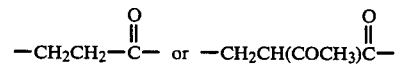

a method analogous to that employed by Bondarenko et al. in Khim. Geterotsikl. Soedin (10) 1387–91 (1981) is utilized. A mixture of 2-methylene-3-quinuclidinone and a 1-(substituted phenyl)-1,3-butanedione are refluxed in acetone. At the completion of the reaction the mixture is poured into cold concentrated hydrochloric acid to provide the triketone

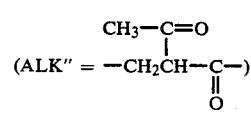

as the hydrochloride salt. Obtention of the diketone

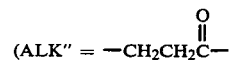

is accomplished by refluxing the triketone in concentrated hydrochloric acid.

The 2-[(substituted phenyl)alkyl]-3-quinuclidinones wherein ALK″ is as defined as 1–4 carbon chain can be prepared by a Grignard reaction. A substituted phenylalkyl halide (substituents being protected where necessary by methods known in the art) is converted to the corresponding Grignard reagent and then is reacted in the presence of a copper halide with 2-methylene-3-quinuclidinone to produce said compounds.

The 2-(arylalkyl)-3-hydroxyquinuclidines may be prepared from the corresponding 2-[(substituted phenyl)alkyl]-3-quinuclidinones by reduction with a suitable hydride reducing agent (lithium aluminum hydride, sodium borohydride, lithium tri-sec-butylborohydride in a known manner.

The various mono or diketones formed in the previous synthetic steps may be reduced to their corresponding methylene compounds, i.e. 2-(arylalkyl)quinuclidines, by employing the Wolff-Kishner reaction. The ketones are reacted with excess hydrazine and potassium hydroxide in ethylene glycol in a well known manner.

Quaternization of the compounds of Formula I to produce the compounds of Formula II can generally be carried out in the following manner. Combine one equivalent of the quinuclidine with at least one or more equivalents of the alkyl halide (or sulfonate). Heat the mixture neat or in a suitable solvent (e.g. acetonitrile, dimethylformamide or nitromethane) at about 40° to 150° C., following the reaction via thin-layer chromatography. At the completion of the reaction the solvent is removed in vacuo. Procedures for isolation of the product will depend on said product and are known in the art. In one such procedure the reaction mixture is dissolved in water and the pH adjusted to about 9 with saturated sodium carbonate. The aqueous solution is then extracted several times with ether, the pH of the aqueous component is adjusted to about 3 with an acid containing the same anion as the quinuclidinium salt. The aqueous layer is extracted with methylene chloride, which is dried and evaporated to obtain the appropriate quinuclidinium salt.

If it is necessary or desirable to change the anion for the compounds of Formula II, this may be accomplished by use of commercially available ion exchange resins. As for instance, the chloride anion may be exchanged on an anion exchange resin (e.g. Biorad AG-1-X8, 20–50 mesh hydroxide form) and the resulting eluates titrated with 10% phosphoric acid to produce the $H_2PO_4^-$ anion.

Method-of-Use and Pharmaceutical Composition Aspect

The compounds of this invention, the quinuclidines, their pharmaceutically acceptable acid addition, quaternary ammonium, or inner salts exhibit cardiovascular properties, that is, they have been found to increase the refractoriness of cardiac tissue, thereby providing their usefulness as antiarrhythmic agents.

Their activity has been analyzed in several procedures such as utilizing standard electrophysiological techniques to measure resting potential, action potential amplitude and duration, rate of rise of phase zero of the action potential and effective refractory periods of normal canine Purkinje fibers; and also utilizing the programmed electrical stimulation conscious dog model.

Thus there is provided by this invention a method for treating arrhythmia which comprises administering to a subject suffering from an arrhythmia or to a subject suspected of developing an arrhythmia an effective amount for treating such arrhythmia of a compound of this invention. The compounds are preferably utilized for the control of re-entrant arrhythmias in humans and for the prevention of sudden death resulting from ventricular fibrillation. Accordingly it is contemplated that the compounds are best utilized in prophylactic treatment. Moreover, since the compounds enhance the electrical stability of the heart, they can be used in conjunction with electrical devices designed to terminate such cardiac arrhythmias, as ventricular tachycardia and ventricular fibrillation.

In general, the compounds of this invention may be administered orally or parenterally. The dosage administered will be dependent on the subject being treated, the route of administration and the type and severity of the arrhythmia being prevented or reduced.

A typical dose for prophylactic treatment, however, will contain from about 0.5 mg/kg to about 10 mg/kg of the active compounds of this invention when administered orally. For I.V. administration, the dose will be from about 0.2 mg/kg to about 4 mg/kg, preferably about 0.2 to about 2 mg/kg.

The compound to be administered can be formulated by admixing with any of a number of suitable pharmaceutical diluents and carriers such as lactose, sucrose, starch powder, cellulose, calcium sulfate, sodium benzoate and the like. Such formulations can be compressed into tablets or can be encapsulated into gelatin capsules for convenient oral administration. Such a capsule may contain one of the compounds of this invention, for example, 2-[3-(4-chlorophenyl)-3-oxopropyl]-1-azabicyclo[2.2.2]octan-3-one hydrochloride in the amount of about 25 to about 500 mg. Such formulation can be administered orally at the rate of about 1 or 2 capsules per day or more often as needed depending upon the particular condition and subject being treated.

For parenteral administration a compound of this invention can be formulated for intramuscular or intravenous administration. In the case of treatment of a patient suffering from a severe cardiac arrhythmia, it may be desirable to administer a compound of the invention by intravenous infusion. The normalized condition can then be maintained by oral administration.

The compounds of this invention can be formulated for parenteral administration with any of a number of pharmaceutically acceptable carriers and diluents to constitute an injectable liquid solution. Commonly used diluents and carriers include water or saline solution, buffered aqueous solutions as well as dispersing and surface active agents if necessary. A typical formulation suited to intramuscular administration may contain one of the compounds of this invention such as 3-[2-(4-chlorophenyl)ethylidene]-1-azoniabicyclo[2.2.2]octane bromide in the amount of about 10 to 250 mg and a solubilizing agent and sufficient sterile water to bring the volume to about 2 ml. Such formulation can be injected at a rate of 1 to 4 times per day or more often depending upon the particular condition of the subject being treated.

The pharmaceutical preparations of the compounds of this invention may optionally, additionally contain one or more other pharmaceutically active substances. Some of the substances envisioned are vasodilators such as glycerol trinitrate, pentaerythritol tetranitrate and carbochromen; diuretic agents, such as chlorothiazide; heart tonics, such as digitalis preparations; hypotensive agents, such as Rauwolfia alkaloids and guanethidine; bronchodilators and sympathomimetic agents, such as isoprenaline, orciprenaline, adrenalin and ephedrine; α-adrenergic blocking agents, such as phentolamine; β-adrenergic blocking agents, such as propranolol and other antiarrhythmic agents such as quinidine.

This invention described hereinabove is illustrated below in the examples, which, however, are not to be construed as limiting the scope of this invention.

PREPARATIONS

General Method for the Conversion of Acid Addition Salts to Free Bases

To 0.02 mole of acid addition salt suspended in 100 ml of ethyl acetate add 30 ml of 5% sodium hydroxide solution. Shake the mixture until all of the solid dissolves, then separate the layers. Extract the aqueous layer with three 50 ml portions of ethyl acetate. Wash the ethyl acetate solutions with 25 ml of water, combine the extracts and dry over anhydrous sodium sulfate.

Filter the drying agent and strip the solvent in vacuo to afford the free base.

General Method for Ion Exchange of Quaternary Salts

For one equivalent of compound to be exchanged, ten equivalents of anion exchange resin (Biorad AG 1-X8, 20–50 mesh, hydroxide form) are used. The resin is stirred in 2N sodium hydroxide aqueous solution (prepared from low chloride sodium hydroxide and deionized water) for 10 minutes, and is filtered and washed with deionized water. The resin is then packed into a column with deionized water and eluted with deionized water until the pH of the eluant is neutral.

An aqueous solution of the compound (if the compound is not water soluble, up to 40% of methanol may be added to obtain a solution) is added to the resin column and is eluted with deionized water. The pH of the eluant is followed, and the fractions having pH above 8 are combined and are washed with diethyl ether three times. Titrate the aqueous hydroxide solution with one equivalent of a 1M solution of the appropriate acid [pH of the solution should be ca. 6.5 after titration with a monobasic acid (e.g. HCl, HBr) and 4.5 after titration with phosphoric acid].

The water is removed either by freeze-drying technique or by propanol azeotrope in vacuo (will depend on the thermal stability of the salt). The crude product can be purified by trituration, recrystallization or other suitable methods.

Preparation 1

[2-(4-Chlorophenyl)ethyl]triphenylphosphonium chloride

Combine 15.0 g (0.086 mole) of 2-(4-chlorophenyl)ethyl chloride and 20.98 g (0.08 mole) of triphenylphosphine. Heat the mixture under a nitrogen atmosphere at 110°–120° C. for 3.5 days. Follow the progress of the reaction by thin layer chromatography on silica gel (hexanes). At the completion of the reaction triturate the resulting solid with 250 ml of anhydrous ether to afford the title compound.

NMR (DMSOd$_6$): δ=2.65–3.27(m, 2), 3.90–4.55(m, 2), 7.15–8.52(m, 19)ppm.

Preparation 2

Diethyl 2-(4-chlorophenyl)ethylphosphonate

Combine 24.9 g (0.15 mole) of triethyl phosphite and 32.9 g of 2-(4-chlorophenyl)ethyl bromide. Heat the mixture at reflux under a nitrogen atmosphere for 5–6 hours. Distill the reaction mixture at reduced pressure (0.2 mm Hg) and collect the fraction distilling at 110°–148° C. to obtain the title compound.

NMR(CDCl$_3$): δ=1.30(t, 6), 1.70–2.40(m, 2), 2.57–3.18(m, 2), 4.10(quin, 4), and 6.95–7.40(m, 4)ppm.

Preparation 3

Diethyl 2-phenylethylphosphonate

In a manner according to Preparation 2 combine 2-phenylethyl bromide and triethyl phosphite. Distill the mixture at reduced pressure (0.15 mm Hg) and collect the fraction distilling at 115°–130° C. to obtain the title compound.

NMR(CDCl$_3$): δ=1.33(t, 6), 1.73–2.43(m, 2), 2.63–3.27(m, 2), 4.13(quin, 4) and 7.17–7.53(m, 5)ppm.

Preparation 4

2-Methylene-3-quinuclidinone

Suspend 95.4 g (0.455 mole) 2-methylene-3-quinuclidinone dihydrate hydrochloride in a solution of 255 g (1.85 moles) anhydrous potassium carbonate dissolved in 350 ml H$_2$O. When the suspension clears add 500 ml methylene chloride and mix the 2-phase system overnight using a mechanical stirrer. Separate the layers and dry the methylene chloride layer over potassium carbonate. Remove the solvents in vacuo to obtain the title compound. Repeat the extraction until most of the product is collected.

NMR(CDCl$_3$): δ=1.65–2.20(m, 4), 2.40–2.70(quin, 1), 2.70–3.45(m, 4), 5.25(s, 1) and 5.75(s, 1)ppm.

Preparation 5

3-(2-Phenylethylidene)-1-azabicyclo[2.2.2]octane hydrochloride

In a manner similar to Example I, Method B, react 3-quinuclidinone with anion generated from diethyl 2-phenylethylphosphonate and n-butyl lithium to provide the title compound and acidify with HCl gas. Collect the title compound via filtration.

NMR(DMSO-d$_6$): δ=1.70–1.94(br s, 4), 1.94–2.24(m, 4), 2.54–2.74(m, 3), 3.18–3.56(m, 4), 4.18(br s, 1), 7.20–7.50(m, 4) and 11.42(br s, 1)ppm.

Preparation 6

2-(3-Phenylpropyl)-1-azabicyclo[2.2.2]octane hydrochloride

To 12.17 g (0.05 mole) of 2-(3-phenylpropyl)-1-azabicyclo[2.2.2]octan-3-one and 25 g (0.5 mole) of 100% hydrazine hydrate in 20 ml of diethylene glycol is added with cooling 11.2 g (0.2 mole) of potassium hydroxide. When the addition is complete heat the mixture under a nitrogen atmosphere at 100°–110° C. for 3–4 hours then gradually raise the temperature to 200° C. and distill off the water and excess hydrazine. Maintain the temperature at 200° C. for 5 hours. Cool the reaction mixture to room temperature and pour onto 100 ml of water. Extract the aqueous mixture with four 150 ml portions of methylene chloride. Combine the extracts and wash with three 75 ml portions of water and one 75 ml portion of saturated sodium chloride solution. Dry the solution over anhydrous sodium sulfate. Filter and remove the solvent in vacuo. Dissolve the residue in 75 ml of 2-propanol and add 5 ml of concentrated hydrochloric acid. Remove the solvent in vacuo to afford the title compound.

EXAMPLES

Example I

3-[2-(4-Chlorophenyl)ethylidene]-1-azabicyclo[2.2.2]octane hydrochloride

Method A.

To 35.0 g (0.08 mole) of [2-(4-chlorophenyl)ethyl]-triphenylphosphonium chloride suspended in 250 ml of anhydrous tetrahydrofuran (THF) under a nitrogen atmosphere cooled to −5° to 0° C. is added 50 ml of 1.77N (0.089 mole) of n-butyl lithium. Stir the solution for one hour and allow to warm to ca. 10° C. To the reaction mixture add dropwise a solution of 10.0 g (0.08 mole) of quinuclidinone in 120 ml of anhydrous THF. Stir the reaction for 1.5 hour and allow the reaction mixture to warm to room temperature. Reflux the reaction mixture for 1 hour. Follow the progress of the reaction by thin-layer chromatography on silica gel (acetone:NH4OH, 95:5). At the completion of the reaction add 50 ml of methanol. Remove the solvent in vacuo and dissolve the residue in 500 ml of toluene. Extract the toluene solution with 4×100 ml of 1N HCl solution. Wash the combined acid extracts with 2×100 ml of diethyl ether. Cool the aqueous solution and collect the solid. Recrystallize the solid from methanol to provide the title compound.

NMR(CF3CO2D): δ=1.65–2.65(m, 4), 3.00–3.90(m, 7), 4.12(br s), 5.73(br t, 1), 6.20–8.90(br, 1) and 6.90–7.50(m, 4)ppm.

Method B.

To 14.53 g (0.05 mole) of diethyl 2-(4-chlorophenyl)-ethylphosphonate in 150 ml of anhydrous dimethoxyethane (DME) under a nitrogen atmosphere cooled to −15-(−10°)C. add 30 ml of 2.36M (0.07 mole) of n-butyl lithium. Stir the solution for one hour then add dropwise a solution of 6.25 g (0.05 mole) of 3-quinuclidinone in 100 ml of anhydrous DME. Allow the stirred solution to warm to room temperature over a period of 1–2 hours then reflux the reaction mixture for one hour. Follow the progress of the reaction by thin-layer chromatography on silica gel (acetonitrile:NH4OH, 9:1). At the completion of the reaction add 5 ml of methanol. Remove the solvent in vacuo and suspend the residue in 250 ml of water. Cool the suspension in an ice/water bath and with good stirring add sufficient hydrochloric acid to bring the mixture to pH 1. Collect the solid by filtration, and triturate the solid with 2-propanol, then recrystallize from methanol to afford the title compound.

Example II

3-[2-(4-Chlorophenyl)ethylidene]-1-heptyl-1-azoniabicyclo[2.2.2]octane bromide

Method A.

Combine 3.60 g (0.015 mole) of 3-[2-(4-chlorophenyl)-ethylidene]-1-azabicyclo[2.2.2]octane and 16.0 g (0.089 mole) of heptyl bromide. Heat the mixture at 115° C. for 10–15 minutes under an atmosphere of nitrogen. Follow the progress of the reaction by thin-layer chromatography on silica gel (acetonitrile:NH4OH, 9:1). At the completion of the reaction, cool the mixture and triturate with 25 ml of diethyl ether. Filter the solid and recrystallize from 2-propanol to provide the title compound.

NMR(DMSO-d6): δ=0.60–2.40(m, 17), 3.00–3.87(m, 9), 4.17(br s, 2), 5.50(br t, 1) and 7.07–7.57(m, 4)ppm.

Method B.

Combine 6.1 g (0.0246 mole) of 3-[2-(4-chlorophenyl)-ethylidene]-1-azabicyclo[2.2.2]octane and 28.0 g (0.155 mole) of heptyl bromide and heat to reflux in 100 ml of tetrahydrofuran under a nitrogen atmosphere. Follow the reaction by thin-layer chromatography on silica gel (methanol:1N NaCl, 95:5). At the completion of the reaction remove the solvent in vacuo. Triturate the residue in ether and filter the solid. Recrystallize the solid from 2-propanol to afford the title compound.

Example III

3-[2-(4-Chlorophenyl)ethyl]-1-heptyl-1-azoniabicyclo[2.2.2]-octane bromide

Combine 2.47 g (0.08 mole) of 3-[2-(4-Chlorophenyl)ethylidene]-1-heptyl-1-azoniabicyclo[2.2.2]octane bromide, 50 ml of acetic acid, 0.26 g of 10% palladium on carbon and 5 ml of water in a Parr bottle and place the mixture on a Parr hydrogenation apparatus. Pressurize the system to 40 p.s.i. and follow the reaction by the pressure drop in the system. Filter the catalyst, remove the solvent in vacuo and triturate the residue with several portions of diethyl ether. Suspend the crude solid in 100 ml of water and adjust the mixture with 10% sodium hydroxide solution to pH 10. Extract the mixture with three 50 ml portions of ether. Adjust the mixture to pH 2 with hydrobromic acid and extract with four 75 ml portions of methylene chloride. Dry the combined organic extracts over anhydrous sodium sulfate. Filter the drying agent and remove the solvent in vacuo. Recrystallize the residue from acetone to obtain the title compound.

NMR(CF3CO2D): δ=0.67–2.37(m, 21), 2.71(t, 2), 2.97–3.80(m, 8) and 7.00–7.47(m, 4)ppm.

Example IV

3-[2-(4-Chlorophenyl)ethyl]-1-azabicyclo[2.2.2]octane hydrochloride

Combine 2.0 g (7 mmole) of 3-[2-(4-chlorophenyl)ethylidene]-1-azabicyclo[2.2.2]octane hydrochloride, 40 ml of acetic acid, 0.2 g of 10% Pd/C catalyst and 5 ml of water. Place the mixture in a Parr apparatus and hydrogenate the mixture at ca. 43 p.s.i. Follow the reaction by the uptake of hydrogen. When the theoretical amount of hydrogen has been absorbed stop the reaction. Remove the catalyst by filtration and wash the catalyst with 40 ml of acetic acid. Remove the solvent from the filtrate in vacuo. Recrystallize the residue from 2-propanol to afford the title compound.

NMR(CF3CO2H): δ=1.60–2.50(m, 8), 2.68(t, 2), 2.90–3.90(m, 6), 6.93–7.40(m, 4) and 6.70–7.97(br, 1)ppm.

Example V

3-[2-(4-Chlorophenyl)ethylidene]-1-methyl-1-azoniabicyclo[2.2.2]octane bromide

To 4.96 g (0.02 mole) of 3-[2-(4-chlorophenyl)ethylidene]-1-azabicyclo[2.2.2]octane in 100 ml of THF is added 5.68 g (0.04 mole) of methyl iodide. Stir the reaction mixture and heat at reflux. Follow the progress of the reaction by thin-layer chromatography on silica gel (methanol:1N NaCl, 95:5). At the completion of the reaction remove the solvent in vacuo to afford the title compound as the iodide salt. The iodide salt is converted to the hydroxide by anion exchange on a column of Biorad AG 1-X8, 20–50 mesh (hydroxide form) resin. The fraction eluting with pH>9 is collected. The aqueous solution containing the hydroxide is titrated to pH=6 with 1N HBr solution. The aqueous solution of the product as the bromide is washed with ether and the water removed in vacuo to afford the title compound.

Example VI

3-[2-(4-Chlorophenyl)ethylidene]-1-(3-sulfopropyl)-1-azoniabicyclo[2.2.2]octane hydroxide, inner salt Combine 7.43 g (0.03 mole) of 3-[2-(4-chlorophenyl)ethylidene]-1-azabicyclo[2.2.2]octane and 5.49 g (0.045 mole) of 1,3-propanesultone in 30 ml of ethanol and heat at reflux for 1-2 hours. Follow the reaction by thin-layer chromatography on silica gel (acetonitrile:N-H$_4$OH, 90:10). At the completion of the reaction cool the mixture to −10° C. Collect the resulting solid by filtration and wash with cold ethanol to provide the title compound.

Example VII

3-[2-(4-Chlorophenyl)ethylidene]-1-[3-((1,1-dimethylethoxy)carbonyl)-2-hydroxypropyl]-1-azoniabicyclo[2.2.2]octane chloride Partially dissolve 3-[2-(4-chlorophenyl)ethylidene]-quinuclidine hydrochloride (0.12 g, 0.5 mmole) in 5 ml of anhydrous methanol and stir under nitrogen atmosphere. Add t-butyl 3,4-epoxybutyrate (0.16 g, 1.0 mmole) and stir at room temperature for three days. Remove methanol in vacuo and purify the residue by preparative thin-layer chromatography on silica gel (acetonitrile: NH$_4$OH, 90:10) to provide the title compound.

NMR(CDCl$_3$): $\delta$=1.42(s, 9), 1.68-2.08(m, 2), 2.08-2.25(m, 2), 2.64(d, 2), 3.09(br s, 1), 3.38(d, 2), 3.42-4.10(m, 7), 4.35(quin, 2), 4.56-4.74(m, 1), 5.55(t, 1), 7.09(d, 2), and 7.18(d, 2)ppm.

Example VIII

3-[2-(4-Nitrophenyl)ethylidene]-1-azabicyclo[2.2.2]octane hydrochloride

To 10.66 g (0.05 mole) of 3-(2-phenylethylidene)-1-azabicyclo[2.2.2]octane dissolved in 100 ml of acetic acid cooled to 12°-15° C. (the acetic acid is just freezing) is added slowly a mixture of 3.75 ml of concentrated sulfuric acid and 3.75 ml of concentrated nitric acid. Stir the cooled reaction for 1 hour, then allow the mixture to warm to room temperature and stir for 2 hours. Follow the reaction by thin-layer chromatography on silica gel (acetonitrile: ammonium hydroxide, 95:5). At the completion of the reaction quench the reaction mixture on 200 ml of ice/water. Keep the aqueous mixture cold and bring to pH>11 by the addition of 20% sodium hydroxide solution. Extract the aqueous mixture with 4×200 ml of methylene chloride. Wash the methylene chloride extracts with 50 ml of water, combine the extracts and dry over anhydrous sodium sulfate. Filter and evaporate the solvent in vacuo to provide the title compound as the free base.

Dissolve the free base in 100 ml of 2-propanol and add 6 ml of concentrated hydrochloric acid. Remove the solvent in vacuo to give the title compound.

EXAMPLE IX

3-[2-(4-Aminophenyl)ethylidene]-1-azabicyclo[2.2.2]octane dihydrochloride

To 7.75 g (0.03 mole) of 3-[2-(4-nitrophenyl)ethylidene]-1-azabicyclo[2.2.2]octane hydrochloride and 7.12 g (0.06 mole) of mossy tin suspended in 50 ml of water add 30 ml (0.36 mole) of concentrated hydrochloric acid in six portions with good mixing. Maintain the reaction just near the boiling point, cooling if necessary. After the reaction slows heat the mixture at 80°-90° C. with good stirring for 1 hour. Follow the progress of the reaction by thin-layer chromatography on silica gel (acetonitrile:ammonium hydroxide, 95:5). At the completion of the reaction cool the mixture to 0°-5° C. Add 20% sodium hydroxide to bring the mixture to pH>12. Filter any solids if necessary and wash the solids well with methylene chloride solution. Extract the aqueous mixture with four 100 ml portions of methylene chloride. Combine the methylene chloride washes and extracts, and wash them with 50 ml of water and 50 ml of saturated sodium chloride solution. Dry the methylene chloride solution over anhydrous sodium sulfate, filter and remove the solvent in vacuo to provide the title compound as the free base.

Dissolve the free base in 50 ml of 2-propanol and add 7 ml of concentrated hydrochloric acid. Remove the solvent in vacuo to give the title compound dihydrochloride.

Example X

N-[4-(2-(1-Azabicyclo[2.2.2]oct-3-ylidene)ethyl)-phenyl]-methanesulfonamide hydrochloride To 4.57 g (0.02 mole) of 3-[2-(4-aminophenyl)ethylidene]1-azabicyclo[2.2.2]octane dissolved in 100 ml of methylene chloride, cooled to −50° C., under a nitrogen atmosphere add dropwise a solution of 2.86 g (0.025 mole) of methanesulfonyl chloride in 25 ml of methylene chloride. After the addition is complete stir the reaction for one-half hour at −50° C. then allow to warm to room temperature. Stir at room temperature for one hour. Follow the progress of the reaction by thin-layer chromatography on silica gel (acetonitrile:ammonium hydroxide, 95:5). At the completion of the reaction add 5 ml of water to the reaction mixture then strip the methylene chloride in vacuo. Add 50 ml of 10% sodium hydroxide. Wash the mixture with three 25 ml portions of ether and one 25 ml portion of methylene chloride. Bring the aqueous base mixture to pH=8-8.5 by the addition of 5% hydrochloric acid solution. Extract the mixture with four 100 ml portions of methylene chloride. Wash the combined methylene chloride extracts with a 50 ml portion of water and then with a 50 ml portion of saturated sodium chloride solution. Dry the methylene chloride extracts over anhydrous sodium sulfate, filter and remove the solvent in vacuo to provide the title compound as the free base.

Dissolve the free base in 50 ml of ethanol and add 4 ml of concentrated hydrochloric acid. Remove the solvent in vacuo to afford the title compound as the hydrochloride.

EXAMPLE XI

3-[2-(4-((methylsulfonyl)amino)phenyl)ethylidene]-1-heptyl-1-azoniabicyclo[2.2.2]octane bromide In a manner similar to Example II, Method A, react N-[4-(2-(1-azabicyclo[2.2.2]oct-3-ylidene)ethyl)-phenyl]methanesulfonamide with heptyl bromide to afford the title compound.

Example XII

3-[2-(4-Chlorophenyl)ethyl]-1-azabicyclo[2.2.2]octane-3-ol hydrochloride

To 2.43 g (0.10 mole) of magnesium in 30 ml of anhydrous tetrahydrofuran under an $N_2$ atmosphere is added slowly 21.95 g (0.10 mole) of 2-(4-chlorophenyl)ethyl bromide. The addition rate is such that a gentle reflux of the solvent is maintained. After the addition is complete the mixture is refluxed until the magnesium metal is thoroughly reacted. Cool the reaction mixture to 40°-45° C. and add a solution of 12.52 g (0.1 mole) of 3-quinuclidinone in 100 ml of anhydrous tetrahydrofuran at a sufficient rate to bring the mixture to a gentle reflux. When the addition is complete reflux the mixture for 1 hour. Follow the progress of the reaction by thin-layer chromatography on silica gel (acetonitrile: ammonium hydroxide, 95:5). At the completion of the reaction cool the mixture to 0°-5° C. in an ice/water bath. Quench the reaction mixture by the slow addition of 20 ml of 10% hydrochloric acid solution. Remove the tetrahydrofuran in vacuo. Add 100 ml of water to the residue then add sufficient 10% sodium hydroxide with cooling to bring the pH of the mixture to 11-12. Remove any magnesium hydroxide which may have precipitated by filtration, then wash the filtered solids with methylene chloride. Extract the aqueous base mixture with three 150 ml portions of methylene chloride. Combine all methylene chloride extracts and wash them with 75 ml of water followed by 75 ml of saturated sodium chloride solution. Dry the methylene chloride solution over anhydrous sodium sulfate. Remove the drying agent by filtration and strip the solvent in vacuo to provide the title compound as the free base.

Dissolve the free base in 150 ml of 2-propanol and add 12 ml of concentrated hydrochloric acid. Remove the solvent in vacuo to provide the title compound hydrochloride.

Example XIII

3-[2-(4-Chlorophenyl)ethyl]-1-heptyl-3-hydroxy-1-azoniabicyclo[2.2.2]octane bromide In a manner similar to Example II, Method B, react 3-[2-(4-chlorophenyl)ethyl]-1-azabicyclo[2.2.2]octan-3-ol with heptyl bromide to afford the title compound.

EXAMPLE XIV

2-[3-(4-Chlorophenyl)propyl]-1-azabicyclo[2.2.2]octan-3-one hydrochloride

To 3.30 g (0.136 mole) magnesium turnings in 50 ml anhydrous diethyl ether under nitrogen, add 28.6 g (0.13 mole) p-chlorophenethyl bromide slowly. Allow the reaction mixture to reflux gently with mechanical stirring for 1½ hours. Chill the reaction mixture on an ice/MeOH bath and add 1.29 g (0.013 mole) copper (I) chloride. Suspend 10.3 g (0.067 mole) 2-methylene-3-quinuclidinone in 30 ml diethyl ether and add dropwise to the chilled reaction mixture. Heat to reflux for an additional 2 hours. Follow progress of the reaction by thin-layer chromatography on silica gel (methanol:N-$H_4OH$, 9:1). When complete, quench the cooled reaction mixture with 25 ml saturated ammonium chloride solution. Filter the 2-phase reaction mixture and separate the layers. Wash the aqueous phase with 1×50 ml diethyl ether. Combine diethyl ether layers and dry over potassium carbonate. Remove solvents in vacuo to obtain the free base of the title compound. Dissolve the residue in 25 ml diethyl ether and acidify with HCl gas. Collect the title compound via filtration.

NMR(DMSO-$d_6$): $\delta$=1.70-1.94(br s, 4), 1.94-2.24(m, 4), 2.54-2.74(m, 3), 3.18-3.56(m, 4), 4.18(br s, 1), 7.20-7.50(m, 4) and 11.42 (br s, 1) ppm.

Example XV

2-[3-(4-nitrophenyl)propyl]-1-azabicyclo[2.2.2]octan-3-one hydrochloride

Nitrate 2-(3-phenylpropyl)-1-azabicyclo[2.2.2]octan-3-one in a manner similar to Example VIII to afford the title compound.

Example XVI

2-[3-(4-Aminophenyl)propyl]-1-azabicyclo[2.2.2]octan-3-one dihydrochloride

To a Parr bottle add 9.74 g (0.03 mole) of 2-[3-(4-nitrophenyl)propyl]-1-azabicyclo[2.2.2]octan-3-one hydrochloride, 150 ml of methanol and 0.5 g of 10% palladium on charcoal catalyst (wet with 2-3 ml of water). Place the bottle on a hydrogenator, flush the system three times with hydrogen and pressurize the system to 25 p.s.i. Shake the reaction mixture and follow the reaction by thin-layer chromatography on silica gel (acetonitrile:ammonium hydroxide, 95:5). At the completion of the reaction remove the catalyst by vacuum filtration. Wash the catalyst with methanol, to the filtrate add 5 ml of concentrated hydrochloric acid. Remove the solvent in vacuo to afford the title compound.

Example XVII

N-[4-(3-(3-Oxo-1-azabicyclo[2.2.2]oct-2-yl)propyl)-phenyl]-methanesulfonamide hydrochloride In a manner similar to Example X, react 2-[3-(4-aminophenyl)propyl]-1-azabicyclo[2.2.2]octan-3-one with methanesulfonyl chloride to afford the title compound.

Example XVIII

1-Heptyl-2-[3-(4-((methylsulfonyl)amino)phenyl)-propyl]-3-oxo-1-azoniabicyclo[2.2.2]octane bromide In a manner similar to Example II, Method A, react N-[4-(3-(3-oxo-1-azabicyclo[2.2.2]oct-2-yl)propyl)-phenyl]-methanesulfonamide with heptyl bromide to yield the title compound.

Example XIX

2-[3-(4-Nitrophenyl)propyl]-1-azabicyclo[2.2.2]octane hydrochloride

Nitrate 2-(3-phenylpropyl)-1-azabicyclo[2.2.2]octane in a manner similar to Example VIII to provide the title compound.

Example XX

2-[3-(4-Aminophenyl)propyl]-1-azabicyclo[2.2.2]octane dihydrochloride

In a manner similar to Example XVI hydrogenate 2-[3-(4-nitrophenyl)propyl]-1-azabicyclo[2.2.2]octane hydrochloride in methanol over palladium on carbon catalyst to provide the title compound.

Example XXI

N-[4-(3-(1-Azabicyclo[2.2.2]oct-2-yl)propyl)phenyl]-methanesulfonamide hydrochloride In a manner similar to Example X react 2-[3-(4-aminophenyl)propyl]-1-azabicyclo[2.2.2]octane with methanesulfonyl chloride to give the title compound.

Example XXII

1-Heptyl-2-[3-(4-((methylsulfonyl)amino)phenyl)-propyl]-1-azoniabicyclo[2.2.2]octane bromide React N-[4-(3-(1-azabicyclo[2.2.2]oct-2-yl)propyl)-phenyl]methanesulfonamide with heptyl bromide in a manner similar to Example II, Method A, to afford the title compound.

Example XXIII

1-Heptyl-2-[3-(4-chlorophenyl)propyl]-3-oxo-1-azoniabicyclo[2.2.2]octane dihydrogen phosphate To 2.20 g (7.9 mmoles) 2-[3-(4-chlorophenyl)propyl]-1-azabicyclo[2.2.2]octan-3-one, add 10 ml (63.6 mmoles) heptyl bromide. Stir and heat at 80°–90° C. for approximately 24 hours. Follow the progress of the reaction by thin-layer chromatography on silica gel (methanol:1M NaCl, 95:5). When reaction is complete, cool and triturate with anhydrous diethyl ether to produce a white precipitate. Dissolve the solid in 15 ml water and pass through a column of 6.0 g Biorad AG 1-X8 20–50 mesh hydroxide form anion exchange resin. Collect and combine aqueous fractions with pH<8. Acidify with phosphoric acid to pH=4.5. Remove the solvents in vacuo to provide the title compound.

NMR(CF$_3$COOD): $\delta$=0.70–1.40(m, 11), 1.40–2.15(m, 4), 2.15–2.60(m, 5), 2.60–3.40(m, 6), 3.40–4.17(m, 5) and 6.95–7.55(m, 4)ppm.

Example XXIV

2-[3-(4-Chlorophenyl)propyl]-1-azabicyclo[2.2.2]octan-3-ol

Suspend 2.4 g (7.8 mmole) of 2-[3-(4-chlorophenyl)-propyl]-1-azabicyclo[2.2.2-octan-3-one hydrochloride in 10 ml methylene chloride. Make basic with ammonium hydroxide and separate the layers. Dry the methylene chloride layer over sodium sulfate. Remove the solvents in vacuo to obtain the ketone as free base. Dissolve the free base in 25 ml THF and stir under N$_2$ in a dry ice/acetone bath. Add dropwise 16 ml 1M L-selectride in THF. Follow progress of reaction by thin-layer chromatography on silica gel (acetonitrile:N-H$_4$OH, 9:1). When complete, quench reaction mixture with 25 ml of water. Acidify to pH=1 with concentrated hydrochloric acid. Extract with 2×25 ml diethyl ether. Make the aqueous layer basic with ammonium hydroxide (pH=11). Extract with 3×25 ml methylene chloride. Dry over sodium sulfate and remove the solvents in vacuo to obtain the title compound. Recrystallize from acetonitrile.

NMR(CDCl$_3$+CF$_3$CO$_2$H): $\delta$=1.52–1.96(m, 6), 1.96–2.20(m, 2), 2.20–2.40(m, 2), 2.50–2.78(m, 2), 3.14–3.58(m, 5), 4.16–4.30(t, 1), 7.00–7.18(d, 2), and 7.18–7.40(d, 2)ppm.

Example XXV 1-(4-Chlorophenyl)-2-[(3-oxo-1-azabicyclo[2.2.2]oct-2-yl)methyl]-1,3-butanedione hydrochloride To a solution of 93.10 g (0.47 mole) 1-(4-chlorophenyl)-1,3-butanedione in 500 ml acetone add 60.0 g (0.39 mole) 2-methylene-3-quinuclidinone. Stir the solution at reflux for about 24 hours. Follow the progress of the reaction by thin-layer chromatography on silica gel (EtOAc:MeOH, 9:1). At the completion of the reaction, chill the solution in an ice/water bath. Acidify dropwise with 35 ml concentrated hydrochloric acid to precipitate the product. Collect the precipitate by filtration to obtain the title compound as a mixture of diastereomers.

NMR(DMSO-d$_6$): $\delta$=1.96–2.34(m, 6), 2.22 and 2.30(singlets, total 3H), 2.56–2.70(m, 1), 3.24–3.68(m, 4), 4.02–4.22(br s, 1), 5.58–5.80(br s, 1), 7.68 and 7.71(doublets, total 2), and 8.08–8.21(doublets, total 2)ppm.

Example XXVI

2-[3-(4-Chlorophenyl)-3-oxopropyl]-1-azabicyclo[2.2.2]octan-3-one hydrochloride

Reflux 105.28 g (0.28 mole) 1-(4-chlorophenyl)-2-[(3-oxo-1-azabicyclo[2.2.2]oct-2-yl)methyl]-1,3-butanedione hydrochloride in 500 ml concentrated hydrochloric acid for 5 hours. Stir with mechanical stirrer. Chill the reaction mixture in an ice bath and collect the title compound via filtration.

NMR(CF$_3$CO$_2$D): $\delta$=2.20–2.64(m, 5), 2.64–2.84(m, 1), 3.04(s, 1), 3.54–3.72(m, 1), 3.72–4.10(m, 5), 4.36–4.54(t, 1), b 7.46–7.74(d, 2) and 7.96–8.20(d, 2) ppm.

Example XXVII

2-[3-(4-Chlorophenyl)propyl]-1-azabicyclo[2.2.2]octane hydrochloride

Combine 15.06 g (0.046 mole) 2-[3-(4-chlorophenyl)-3-oxopropyl]-1-azabicyclo[2.2.2]octane-3-one hydrochloride, 45 ml (0.93 mole) hydrazine monohydrate, 50.6 g (0.9 mole) potassium hydroxide and 75 ml diethylene glycol and heat to 100° C. After 3 hours, fit the reaction flask with a distillation head and heat reaction in an oil bath until oil bath temperature reaches approximately 190° C. Heat at this temperature for 5 hours. Cool the reaction mixture to room temperature. Quench the cool mixture with 500 ml H$_2$O. Adjust the pH with concentrated hydrochloric acid to pH=1. Wash the aqueous layer 1×250 ml diethyl ether. Adjust pH of the aqueous layer to pH=11 with ammonium hydroxide. Extract with 3×250 ml methylene cloride. Dry the extracts over potassium carbonate, filter and remove the solvents in vacuo to obtain 2-[3-(4-chlorophenyl)-propyl]-1-azabicyclo[2.2.2]octane as an oil. Dissolve this oil in 50 ml ethanol and acidify with HCl gas. Remove the solvents in vacuo to obtain an oil. Triturate the residue in diethyl ether to obtain the title compound. Recrystallize product from 2-propanol.

NMR(DMSO-d$_6$): $\delta$=1.28–1.44(m, 2), 1.44–2.16(m, 8), 2.52–2.68(t, 2), 2.96–3.54(m, 6), and 7.22–7.44(m, 4)ppm.

Example XXVIII

1-[3-Carboxy-1-hydroxypropyl]-3-[2-(4-chlorophenyl)ethylidene]-1-azoniabicyclo[2.2.2]octane hydroxide, inner salt Stir 4.42 g (0.01 mole) of 3-[2-(4-chlorophenyl)ethylidene]-1-[3-((1,1-dimethylethoxy)carbonyl)-2-hydroxypropyl]-1-azoniabicyclo[2.2.2]octane chloride in 25 ml of trifluoroacetic acid. Follow the progress of the reaction by thin-layer chromatography on silica gel. When the reaction is complete (ca. 3–5 hr) remove the solvent in vacuo. Dissolve the residue in methanol/water. Stir the aqueous methanol solution with sufficient anion exchange resin (Biorad AG-1-X8, hydroxide form) to bring the pH of the solution to pH=9. Remove the resin by filtration and evaporate the solvent in vacuo at room temperature to provide the title compound.

Example XXIX 1-(4-Chloro-3-nitrophenyl)-2-[(3-oxo-1-azabicyclo[2.2.2]oct-2-yl)methyl]-1,3-butanedione hydrochloride In a manner similar to Example XXV react 1-(4-chloro-3-nitrophenyl)-1,3-butanedione with 2-methylene-3-quinuclidinone in acetone to provide the title compound.

Example XXX

2-[3-(4-Chloro-3-nitrophenyl)-3-oxopropyl]-1-azabicyclo[2.2.2]octan-3-one hydrochloride In a manner similar to Example XXVI react 1-(4-chloro-3-nitrophenyl)-2-[(3-oxo-1-azabicyclo[2.2.2]oct-2-yl)methyl]-1,3-butanedione hydrochloride in refluxing concentrated hydrochloric acid to afford the title compound.

Example XXXI

2-[3-(3-Amino-4-chlorophenyl)-3-oxopropyl]-1-azabicyclo[2.2.2]octan-3-one dihydrochloride Hydrogenate 11.2 g (0.03 mole) of 2-[3-(4-chloro-3-nitrophenyl)-3-oxopropyl]-1-azabicyclo[2.2.2]octan-3-one hydrochloride over 1.5 g of 10% palladium on carbon catalyst in 250 ml of ethanol. Follow the progress of the reaction by hydrogen uptake and by thin-layer chromatography. When the reaction is complete remove the catalyst by filtration. To the filtrate add 5 ml of concentrated hydrochloric acid. Remove the solvent in vacuo to give the title compound.

Example XXXII

2-[3-(4-Chloro-3-((methylamino)carbonylamino)-phenyl)-3-oxopropyl]-1-azabicyclo[2.2.2]octan-3-one hydrochloride To 6.14 g (0.02 mole) of 2-[3-(3-amino-4-chlorophenyl)-3-oxopropyl]-1-azabicyclo[2.2.2]octan-3-one in 150 ml of methylene chloride add 1.20 g (0.021 mole) of methyl isocyanate. Stir the reaction mixture at room temperature and follow the progress of the reaction by thin-layer chromatography. At the completion of the reaction remove the solvent in vacuo. Dissolve the residue in 100 ml of ethanol and add 2.5 ml of concentrated hydrochloric acid. Remove the solvent in vacuo to obtain the title compound.

Example XXXIII

N-[2-Chloro-5-[3-(3-oxo-1-azabicyclo[2.2.2]oct-2-yl)-1-oxopropyl]phenyl]methanesulfonamide hydrochloride To 6.14 g (0.02 mole) of 2-[3-(3-amino-4-chlorophenyl)-3-oxopropyl]-1-azabicyclo[2.2.2]octan-3-one in 100 ml of chloroform add 5.22 g (0.03 mole) of methanesulfonic anhydride. Heat the mixture to reflux and follow the progress of the reaction by thin-layer chromatography. At the completion of the reaction add 100 ml of water and stir for ca. ½ hour. Adjust the pH of the water layer to pH=8.5–9 with sodium carbonate. Separate the layers and extract the water layer with 4×100 ml of chloroform. Combine the chloroform extracts and dry over anhydrous sodium sulfate. Remove the drying agent by filtration and evaporate the solvent in vacuo. Dissolve the residue in 100 ml of ethanol and add 2.5 ml of concentrated hydrochloric acid. Remove the solvent in vacuo to afford the title compound.

Example XXXIV 1-(4-Nitrophenyl)-2-[(3-oxo-1-azabicyclo[2.2.2]oct-2-yl)methyl]-1,3-butanedione hydrochloride In a manner similar to Example XXV substituting 1-(4-nitrophenyl)-1,3-butanedione for 1-(4-chlorophenyl)-1,3-butanedione prepare the title compound.

NMR (DMSO-d$_6$): $\delta$=1.94–2.40(m, 6), 2.24 and 2.34(singlets, total 3H), 2.56–2.72(m, 1), 3.24–3.74(m, 4), 4.18(br s, 1), 5.80(br s, 1), 8.16–8.44(m, 4) and 11.75(br s, 1)ppm.

Example XXXV

2-[3-(4-Nitrophenyl)-3-oxopropyl]-1-azabicyclo[2.2.2]octan-3-one hydrochloride

In a manner similar to Example XXVI substituting the product of Example XXXIV for Example XXV, prepare the title compound.

NMR (DMSO-d$_6$): $\delta$=2.00–2.28(m, 4), 2.28–2.46(m, 1), 2.62(br s, 1), 3.20–3.80(m, 7), 4.16–4.32(br s, 1), 8.20–8.30(d, 2), 8.38–8.48(d, 2) and 13.50(br s, 1)ppm.

I claim:

1. A compound of the formula I:

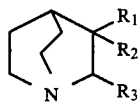

I wherein
$R_1$ is H or OH;
$R_2$ is H or ALK—Z;
$R_1$, $R_2$ taken together form =O or =CH—ALK'—Z;
$R_3$ is H or —ALK"—Z;
where
ALK is a straight chain alkyl of 2–4 carbon atoms;
ALK' is a straight chain alkyl of 1–3 carbon atoms;
ALK" is a straight chain alkyl of 1–4 carbon atoms,

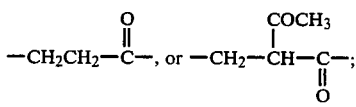

Z is

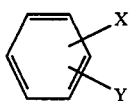

where X and Y are the same or independently hydrogen, halogen, hydroxyl, loweralkyl, loweralkoxy, amino, cyano, nitro, loweralkanecarboxamido, loweralkanesulfonamido, carbamoyl, loweralkylcarbamoyl, loweralkylsulfonyl, sulfamoylamino, N-loweralkylsulfamoyl, trifluoromethanesulfonamido, ureido or N-loweralkylureido;
with the provisos that:
(a) X and Y cannot both be hydrogen,
(b) $R_2$ and $R_3$ cannot both be hydrogen,
(c) when $R_3$ is —ALK"—Z wherein the ALK" is —CH$_2$—CH(COCH$_3$)—CO— or —CH$_2$CH$_2$CO— then together $R_1$ and $R_2$ must be =O,
(d) when $R_3$ is —ALK"—Z wherein the ALK" is a straight chain alkyl of 1–4 carbon atoms then $R_2$ cannot be —ALK—Z, and $R_1$, $R_2$ together cannot be =CH—ALK'-Z,
(e) when $R_1R_2$ taken together form =O then $R_3$ cannot be hydrogen or a pharmaceutically acceptable acid addition salt thereof;
or a quaternary ammonium salt thereof of the formula II

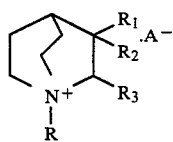

II wherein
$R_1$, $R_2$, $R_3$ are as above, and
R is a straight or branched chain alkyl of 1–12 carbon atoms, cycloalkyl(lower)alkyl, phenyl(lower)alkyl, —CH$_2$CHOHCH$_2$W, —(CH$_2$)$_m$—W or —(CH$_2$)$_m$SO$_3$H;
where
m is an integer of 1–5;
W is COO—V;
where V is hydrogen or a straight or branched chain alkyl of 1–4 carbon atoms,
with the proviso that when R is a straight or branched chain alkyl, the carbon atom alpha to the nitrogen is primary, and
A is an anion forming a pharmaceutically acceptable salt;
or the inner salt of formula II, formed when the anion A is R when R is —CH—CHOH—CHCOO$^-$, —(CH$_2$)$_m$—COO$^-$, or —(CH$_2$)$_m$SO$_3^-$
where m is as previously described.

2. A compound of claim 1 wherein $R_1$, $R_2$ together form =O.

3. A compound of claim 1 wherein $R_3$ is —ALK"—Z.

4. A compound of claim 1 wherein X and Y are the same or independently hydrogen, halogen, hydroxyl, loweralkoxy, loweralkanesulfonamido or N-loweralkylureido.

5. A compound of claim 1 wherein $R_1$, $R_2$ together form =O, $R_3$ is —ALK"—Z, X and Y are the same or independently hydrogen, halogen, hydroxyl, lower alkoxy, loweralkanesulfonamido or N-loweralkylureido.

6. A compound of claim 5 wherein —ALK"—Z is —CH$_2$CH$_2$—CH$_2$—Z or

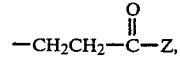

and wherein X and Y are the same or independently hydrogen, halogen, or loweralkanesulfonamido.

7. A compound of claim 6 wherein X and Y are the same or independently hydrogen, chlorine, or methanesulfonamide.

8. A compound of claim 7 wherein, when one of X or Y is chlorine or methanesulfonamide, it is located in the para-position.

9. A compound of claim 1 which is 3-[2-(4-chlorophenyl)ethylidene]-1-azabicyclo[2.2.2]octane hydrochloride.

10. A compound of claim 1 which is 3-[2-(4-chlorophenyl)ethylidene]-1-heptyl-1-azoniabicyclo[2.2.2]octane bromide.

11. A compound of claim 1 which is 3-[2-(4-chlorophenyl)ethyl]-1-heptyl-1-azoniabicyclo[2.2.2]octane bromide.

12. A compound of claim 1 which is 2-[3-(4-chlorophenyl)propyl]-1-azabicyclo[2.2.2]octan-3-ol.

13. A compound of claim 1 which is 2-[3-(4-chlorophenyl)propyl]-1-azabicyclo[2.2.2]octane hydrochloride.

14. A compound of claim 1 which is 3-[2-(4-chlorophenyl)ethylidene]-1-[3-((1,1-dimethylethoxy)carbonyl)-2-hydroxypropyl]-1-azoniabicyclo[2.2.2]octane chloride.

15. A compound of claim 1 which is 3-[2-(4-chlorophenyl)ethyl]-1-azabicyclo[2.2.2]octane hydrochloride.

16. A compound of claim 1 which is 3-[2-(4-chlorophenyl)ethylidene]-1-methyl-1-azoniabicyclo[2.2.2]octane bromide.

17. A compound of claim 1 which is 3-[2-(4-chlorophenyl)ethylidene]-1-(3-sulfopropyl)-1-azoniabicyclo[2.2.2]octane hydroxide, inner salt.

18. A compound of claim 1 which is 1-(3-carboxy-2-hydroxypropyl)-3-[2-(4-chlorophenyl)ethylidene]-1-azoniabicyclo[2.2.2]octane hydroxide, inner salt.

19. A compound of claim 1 which is 3-[2-(4-nitrophenyl)ethylidene]-1-azabicyclo[2.2.2]octane hydrochloride.

20. A compound of claim 1 which is 3-[2-(4-aminophenyl)ethylidene]-1-azabicyclo[2.2.2]octane dihydrochloride.

21. A compound of claim 1 which is N-[4-(2-(1-azabicyclo[2.2.2]oct-3-ylidene)ethyl)phenyl]methanesulfonamide hydrochloride.

22. A compound of claim 1 which is 3-[2-(4-((methylsulfonyl)amino)phenyl)ethylidene]-1-heptyl-1-azoniabicyclo[2.2.2]octane bromide.

23. A compound of claim 1 which is 3-[2-(4-chlorophenyl)ethyl]-1-azabicyclo[2.2.2]octane-3-ol hydrochloride.

24. A compound of claim 1 which is 3-[2-(4-chlorophenyl)ethyl]-1-heptyl-3-hydroxy-1-azoniabicyclo[2.2.2]octane bromide.

25. A compound of claim 1 which is 2-[3-(4-nitrophenyl)propyl]-1-azabicyclo[2.2.2]octane hydrochloride.

26. A compound of claim 1 which is 2-[3-(4-aminophenyl)propyl]-1-azabicyclo[2.2.2]octane dihydrochloride.

27. A compound of claim 1 which is N-[4-(3-(1-azabicyclo[2.2.2]oct-2-yl)propyl)phenyl]methanesulfonamide hydrochloride.

28. A compound of claim 1 which is 1-heptyl-2-[3-(4-((methylsulfonyl)amino)phenyl)propyl]-1-azoniabicyclo[2.2.2]octane bromide.

29. A compound of claim 2 which is 2-[3-(4-nitrophenyl)propyl]-1-azabicyclo[2.2.2]octan-3-one hydrochloride.

30. A compound of claim 2 which is 2-[3-(4-aminophenyl)propyl]-1-azabicyclo[2.2.2]octan-3-one dihydrochloride.

31. A compound of claim 5 which is 1-(4-chlorophenyl)-2-[(3-oxo-1-azabicyclo[2.2.2]oct-2-yl)methyl]-1,3-butanedione hydrochloride.

32. A compound of claim 6 which is N-[4-(3-(3-oxo-1-azabicyclo[2.2.2]oct-2-yl)propyl)phenyl]methanesulfonamide hydrochloride.

33. A compound of claim 6 which is 1-heptyl-2-[3-(4-((methylsulfonyl)amino)phenyl)propyl]-3-oxo-1-azoniabicyclo[2.2.2]octane bromide.

34. A compound of claim 6 which is N-[2-chloro-5-[3-(3-oxo-1-azabicyclo[2.2.2]oct-2-yl)-1-oxopropyl]-phenyl]methanesulfonamide hydrochloride.

35. A compound of claim 8 which is 2-[3-(4-chlorophenyl)-3-oxopropyl]-1-azabicyclo[2.2.2]octan-3-one hydrochloride.

36. A compound of claim 8 which is 2-[3-(4-chlorophenyl)propyl]-1-azabicyclo[2.2.2]octan-3-one hydrochloride.

37. A compound of claim 8 which is 1-heptyl-2-[3-(4-chlorophenyl)propyl]-3-oxo-1-azoniabicyclo[2.2.2]octane dihydrogen phosphate.

38. A pharmaceutical composition for treating arrhythmias comprising an antiarrhythmically effective amount of a compound of claim 1 together with a nontoxic pharmaceutically acceptable carrier.

39. The method of treating arrhythmias in a mammalian subject in need thereof comprising administering to said subject an antiarrhythmically effective dose of a compound according to claim 1.

* * * * *